United States Patent [19]

Fergason et al.

[11] Patent Number: 5,074,647
[45] Date of Patent: Dec. 24, 1991

[54] LIQUID CRYSTAL LENS ASSEMBLY FOR EYE PROTECTION

[75] Inventors: Jeffrey K. Fergason, Menlo Park; John D. Fergason, Sunnyvale, both of Calif.

[73] Assignee: Optical Shields, Inc., Menlo Park, Calif.

[21] Appl. No.: 447,297

[22] Filed: Dec. 7, 1989

[51] Int. Cl.$^5$ .............................................. G02F 1/13
[52] U.S. Cl. ........................................ 359/63; 359/93; 359/84; 359/98
[58] Field of Search ................. 350/331 R, 334, 337, 350/347 E

[56] References Cited

U.S. PATENT DOCUMENTS

| Re. 29,684 | 6/1978 | Gordon | 350/331 R |
|---|---|---|---|
| Re. 32,521 | 10/1987 | Fergason | 350/334 |
| 2,548,230 | 4/1951 | Molineux | 88/61 |
| 3,159,844 | 12/1964 | Haboush | 2/8 |
| 3,245,315 | 4/1966 | Marks | 350/331 R |
| 4,039,254 | 8/1977 | Harsch | 350/335 |
| 4,240,709 | 12/1980 | Hornell | 350/335 |
| 4,385,806 | 5/1983 | Fergason | 350/347 R |
| 4,435,047 | 3/1984 | Fergason | 350/334 |
| 4,436,376 | 3/1984 | Fergason | 350/332 |
| 4,540,243 | 9/1985 | Fergason | 350/337 |
| 4,556,289 | 12/1985 | Fergason | 350/350 R |
| 4,728,173 | 3/1988 | Toth | 350/332 |
| 4,813,766 | 3/1989 | Keene et al. | 350/337 |
| 4,877,310 | 10/1989 | Seachman et al. | 350/347 E |
| 4,928,181 | 5/1990 | Harward | 350/337 X |

OTHER PUBLICATIONS

Pending U.S. patent appln. Ser. No. 259,951, filed 10/19/88.
Pending U.S. patent appln. Ser. No. 261,045, filed 10/21/88.
Pending U.S. patent appln. Ser. No. 365,167, filed 6/12/89.

*Primary Examiner*—Stanley D. Miller
*Assistant Examiner*—Huy K. Mai
*Attorney, Agent, or Firm*—Renner, Otto, Boisselle & Sklar

[57] ABSTRACT

A light control device includes a light shutter having a pair of polarizers and a liquid crystal device operative in response to a prescribed input to control transmission of light therethrough, and a variable polarizer optically aligned with respect to said light shutter and operative to control light transmitted therethrough in response to a prescribed input; the light shutter is operative relatively fast in response to application of electric field to reduce light transmission and the variable polarizer is operative in the event of a power loss, which would cause the light shutter to stop light blocking, to provide a safety light blocking function. The light control device may be employed in a welding helmet or other device intended to provide protection to the eyes of an individual or other animate or inanimate object from selected electromagnetic energy, such as that produced by welding or other source.

39 Claims, 2 Drawing Sheets

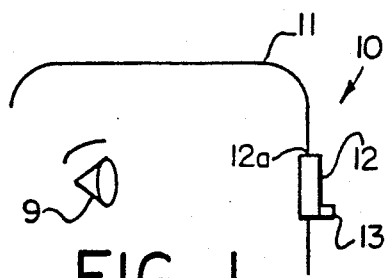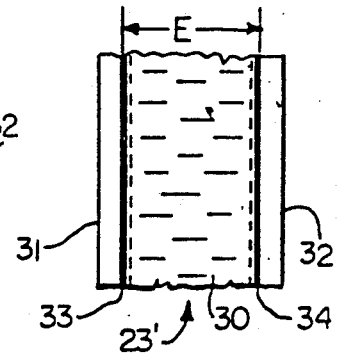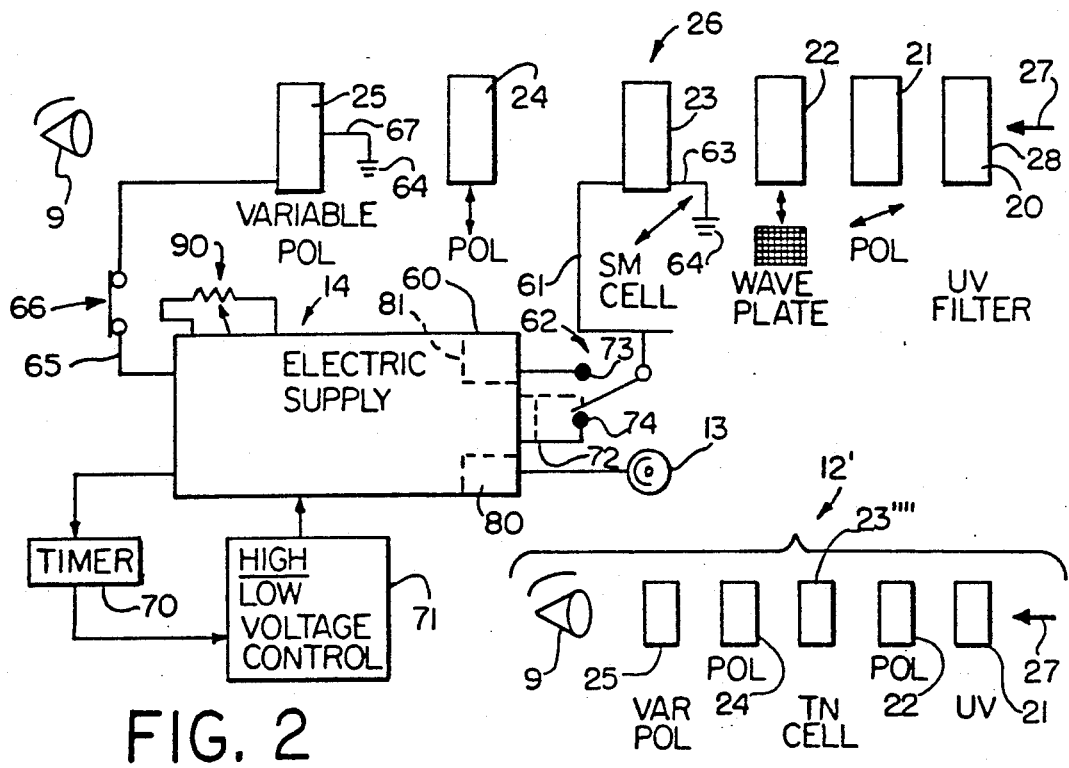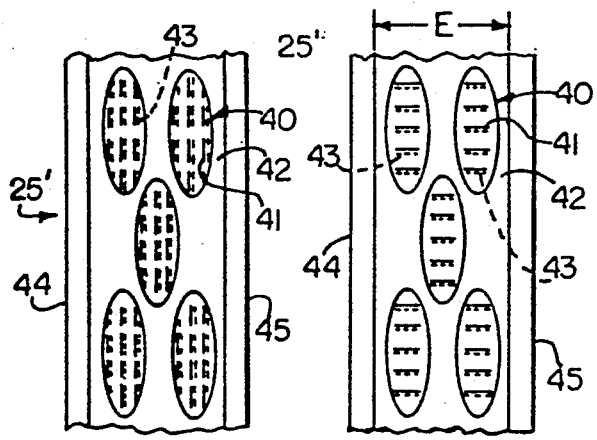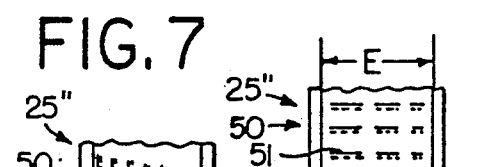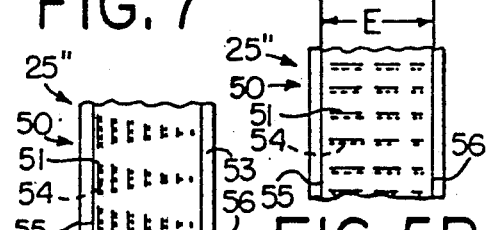

LIQUID CRYSTAL LENS ASSEMBLY FOR EYE PROTECTION

TECHNICAL FIELD

The present invention relates generally, as is indicated, to electro-optic shutters, and, more particularly, to high speed electro-optic shutters for controllably blocking or transmitting light and having a partial blocking condition in a failure mode.

BACKGROUND

A number of devices known as liquid crystal devices for controlling transmission or characteristics of light are, of course, known. For convenience such devices will be referred to as light shutters, although the actual "shuttering", i.e., light transmitting and/or blocking functions may be effected by the combination of the liquid crystal device and one or more polarizers and/or other devices associated therewith. Moreover, although a light shutter is preferably a device that provides control of light transmission over a relatively large area as compared to a display in which light may be controlled on a segment by segment (e.g., as in a conventional seven segment display configuration) and/or in a dot by dot arrangement, it is to be understood that the concepts of the invention may be employed in such displays and the like on a scale that is smaller than the relatively large area to which a shutter often relates. Therefore, the term shutter hereinafter is intended to include both such relatively large area devices and smaller area devices that control transmission of light therethrough. Also, the terms liquid crystal cell and liquid crystal device may be used synonymously herein One exemplary type of liquid crystal devices or light shutters that are known are referred to, for example, as twisted nematic liquid crystal device, cell, shutter, etc. In such a twisted nematic device incident plane polarized light may be transmitted directly through the liquid crystal device without any substantial change in the optical sense when an electric field is applied across the liquid crystal material However, in the absence of the field the liquid crystal causes the plane of polarization to rotate, e.g., by 90 degrees. With the twisted nematic liquid crystal device between a pair of crossed or parallel plane polarizers, then, light transmitted through the assemblage thereof can be controlled as a function of whether or not the electric field is applied across the liquid crystal material in the liquid crystal device.

Another exemplary known liquid crystal device is that sometimes referred to as a birefringent liquid crystal device. In such birefringent liquid crystal devices, due to the birefringent effect and, thus, the retardation of one of the quadrature components of plane polarized light relatively to the other (e.g., the ordinary and extraordinary ray components of such polarized light) as a function of alignment of liquid crystal structure in the liquid crystal device, the direction of plane polarization of light transmitted through such device can be altered, e.g., rotated. Such alteration, or rotation, may be a function of whether or not an electric field input is applied to the liquid crystal material in the device and the magnitude of such an applied field.

An example of a birefringent liquid crystal device is presented in U.S. Pat. Nos. 4,385,806, Re 32,521 and 4,540,243.

The invention as is described further below may be employed with the foregoing and other types of liquid crystal light shutters.

Although the above-described liquid crystal light shutters are of the type which respond to application or not of electric field, it will be appreciated that other types of input may be supplied to the liquid crystal material, such as thermal inputs, magnetic field inputs, etc. consistent with the present invention. Therefore, reference to application of electric field may be considered to include application of another appropriate input that will cause a light transmission controlling function or the like, such as a change in the intensity of light transmitted through the device to which the input is applied.

The invention also employs use of a variable polarizer or controllable polarizer type of device One example of a variable polarizer is a twisted nematic liquid crystal cell which employs pleochroic (or dichroic) dye that aligns with the liquid crystal material in the device in what is known as guest host relationship. In such a variable polarizer, in the absence of an electric field, for example, the liquid crystal material causes alignment of the dye to cause the dye to operate as a plane polarizer. In the presence of such a field the liquid crystal material aligns with the field, for example, and causes the dye also to align therewith so that the dye stops polarization function or ceases to exhibit characteristics of a plane polarizer.

Another type of variable polarizer is disclosed in copending U.S. patent applications Ser. No. 259,951 filed Oct. 19, 1988 and 261,045 filed Oct. 21, 1988. Such a variable polarizer also may be employed in the present invention, as may other types of variable polarizers.

Various devices have been employed in the past to protect the eyes of a person (or to protect some other animate or inanimate object) from particular types of electromagnetic energy or radiation. Exemplary devices are welding helmet devices or goggles to protect the eyes of an individual from the light or other electromagnetic energy emitted during a welding process, goggles or the like to protect the eyes from flash blindness, and/or to protect the eyes, for example, from other sources of bright light, etc. Several exemplary eye protection devices include those disclosed in U.S. Pat. Nos. 3,245,315, Re 29,684, and 4,039,254 and U.K. patent 565,395. Other electromechanically operated light shutter devices are disclosed in U.S. Pat. Nos. 2,548,230 and 3,159,844.

The disclosures of the above-mentioned patents and patent applications are hereby entirely incorporated by reference.

In a conventional liquid crystal device used as a light shutter or for some other purpose, the application of a voltage from which an electric field is derived to the liquid crystal device can be used to cause a dark to clear transition or a clear to dark transition, depending on the orientation of the usual pair of plane polarizers associated with the liquid crystal device, e.g., between which the liquid crystal device usually is positioned. When voltage is increased from a low level (or no applied voltage) to a higher voltage, the liquid crystal directors are driven by the electric field to an "energized" alignment condition, which typically is an alignment that is perpendicular to the surfaces (sometimes referred to as the substrate surfaces) between which the liquid crystal material forming the liquid crystal device is contained. When the voltage is reduced or eliminated, the liquid crystal directors relax to their natural alignment, e.g., generally in parallel with the substrate surfaces or partly in parallel therewith. The voltage applies a much greater force than the relaxation conditions do to the directors, e.g., due to interaction with the surfaces and/or coatings thereon, the tendency of the liquid crystal (especially nematic liquid crystal) to align in a linear fashion, etc., and, therefore, causes the directors to align with respect to the field much faster than the time required for natural relaxation.

In a welding system, and perhaps in other circumstances, it is desirable, sometimes critical, that the switching speed of a shutter device to go from a so-called unprotected mode to a protected mode is particularly very fast, especially in an automatic shutter device. For example, in a welding helmet application, it is important that the switching speed of an automatic liquid crystal shutter device (e.g., controlled to darkened condition automatically in response to sensing of the ignition of the welding arc or the like) be fastest when the liquid crystal device is changing from the clear condition transmitting light to the dark condition to block light. This fast operation helps to assure that the dark condition will exist as promptly as is possible after the welding arc has been ignited. Therefore, it is most appropriate to configure the liquid crystal device, particularly the liquid crystal device in combination with the associated polarizers, in such manner that the dark condition is achieved by applying a voltage. Thus, the clear condition would occur when voltage is removed or is substantially reduced relative to the voltage applied to achieve the dark condition.

Causing the liquid crystal shutter to operate in the manner just described above may tend to cause a different problem. In particular, the clear condition would be achieved by removing the voltage from the liquid crystal device. Unfortunately, though, if there were a system failure, such as a circuit failure or a power supply (e.g., battery) failure, the liquid crystal device would fail to a clear condition creating the risk for eye injury if the failure were to occur during a welding operation or during some other condition during which it is desirable to provide a darkened, i.e., reduced light transmission, condition of the liquid crystal shutter.

One prior technique for preventing such a failure mode condition has used two twisted nematic liquid crystal cells with polarizers aligned in such a way that a failure would result in a partial light blocking condition. Such a system, though, requires a minimum of two liquid crystal cells and three or more polarizers. Liquid crystal systems with this construction contain more components, are more expensive to manufacture, have a narrow dynamic optical range and have limited speed compared to the present invention, which will be described in further detail below. Moreover, the two liquid crystal cell construction of such prior technique has employed plastic polarizers on the outer surfaces of the cell construction which are difficult to clean without damage and can delaminate in harsh environments. The present invention also overcomes these problems of the prior art.

SUMMARY

The invention provides the ability for a liquid crystal light control device to operate at relatively fast speeds, e.g. to be driven to the dark or reduced light transmission condition, in less than one millisecond, and provides an intermediate light transmission condition in the event of a power off failure mode of operation or condition so that reduced light transmission operation can be continued while a welding operation, for example, is completed.

According to the invention a liquid crystal light control device is operative at relatively fast speeds, e.g. to be driven to the dark or reduced light transmission condition, in less than one millisecond, provides an intermediate light transmission condition in the event of a power off failure mode of operation or condition so that reduced light transmission operation can be continued, e.g., while a welding operation is completed, and provides a maximum light transmission condition when power is supplied at the same time that welding operation or some other condition that would call for reduced light transmission mode of operation is not occurring.

Briefly, according to one aspect of the invention, a light shutter includes a pair of polarizers and a liquid crystal device operative in response to a prescribed input to control transmission of light therethrough, and a variable polarizer optically aligned with respect to said light shutter and operative to control light transmitted therethrough in response to a prescribed input.

According to another aspect, a welding helmet includes a protective shield, and a light control device, the light control device includes a light shutter including a pair of polarizers and a liquid crystal device operative in response to a prescribed input to control transmission of light therethrough, and a variable polarizer optically aligned with respect to said light shutter and operative to control light transmitted therethrough in response to a prescribed input.

According to another aspect an eye protection apparatus includes a lens assembly for positioning in front of the eyes, said lens assembly including a light shutter having a pair of polarizers and a liquid crystal device operative in response to a prescribed input to control transmission of light therethrough, and a variable polarizer optically aligned with respect to said light shutter and operative to control light transmitted therethrough in response to a prescribed input.

According to another aspect a method for protecting the eyes of an individual, includes directing light to a light shutter which includes a pair of polarizers and a liquid crystal device, supplying a prescribed input to control transmission of light through such device, and directing light transmitted through such light shutter through a variable polarizer operative to control light transmitted therethrough in response to a prescribed input.

Another aspect of the invention relates to an electronic drive circuit that provides a relatively high voltage to the liquid crystal cell in a light shutter for a relatively short period of time as the liquid crystal cell is switched from a transmitting condition to a reduced light transmission condition in order to cause maximum force on the liquid crystal directors causing high speed reorientation Thereafter, e.g., after a few milliseconds or a few microseconds, the voltage may be reduced to a level that sustains the desired optical density, shade or light transmission condition. This feature tends to speed switching time while prolonging the life of a battery employed to supply electrical power to the liquid crystal cell.

Another aspect of the invention relates to an electronic drive circuit that provides a relatively high voltage pulse to the liquid crystal cell in a light shutter for a sufficient duration to effect desired high speed reorientation of liquid crystal structure or directors and thereafter voltage may be reduced to a sustaining level to maintain the reoriented alignment.

According to another aspect, an electric circuit is provided for a liquid crystal shutter wherein the circuit is adjustable to alter the voltage applied to the liquid crystal shutter thereby to select specified shades or shade levels of light transmission operation thereof.

According to another aspect, a light control device includes a light shutter having a pair of polarizers and a liquid crystal device operative in response to a prescribed input to control transmission of light therethrough, and a variable liquid crystal device optically aligned with respect to the light shutter and operative to control light transmitted therethrough in response to a prescribed input and including a plurality of volumes of liquid crystal material in a containment medium operative to effect scattering or absorption of light in the absence of a field input and to reduce such scattering or absorption in the presence of such field input.

According to the invention operation to obtain protection for the eyes of an individual or for some other animate or inanimate object is achieved at high speed while providing a very high optical range. The view provided during the various modes of operation is very clear with minimum distortion and the device in the darkened mode of operation attenuating light or reducing transmission is very dark.

Moreover, operation to attenuate light in the preferred embodiment described in detail preferably is on the order of shade number 10, 11, 12 or 13 in the darkened mode and in the failure mode is within about four shades of the darkest shade that is provided in the darkened mode. Thus, operation of the invention provides for relatively dark or relatively bright light transmission conditions when power is proper, depending on whether or not a darkened condition is called for; and operation in a power failure mode provides an intermediate level of darkness, as is described in further detail herein.

These and other objects, advantages and features of the present invention will become evident to those of ordinary skill in the art after having read the following detailed description of the preferred embodiment. It will be understood that although a preferred embodiment is described in detail, the scope of the invention is to be limited only by the claims.

BRIEF DESCRIPTION OF THE DRAWING

In the annexed drawing,

FIG. 1 is a schematic illustration of a welding helmet or exemplary type of eye protection apparatus in accordance with the preferred embodiment and best mode of the present invention;

FIG. 2 is a schematic illustration of a light controlling lens assembly employed in the welding helmet of FIG. 1;

FIGS. 3A and 3B are schematic illustrations of one form of surface mode birefringent liquid crystal light control shutter device according to the invention, respectively, in non-energized plane polarized light rotating mode and in energized non-rotating mode;

FIGS. 4A and 4B are schematic illustrations of one form of variable polarizer according to the invention, respectively, in polarizing and non-polarizing modes;

FIGS. 5A and 5B are schematic illustrations of a dyed twisted nematic liquid crystal variable polarizer, respectively, in polarizing and non-polarizing modes; and FIGS. 6A and 6B are schematic illustrations of an NCAP type of nematic liquid crystal variable polarizer, respectively, in light blocking or scattering and light transmitting modes;

FIG. 7 is a schematic illustration of a modified light controlling lens assembly employable in the welding helmet of FIG. 1 using a twisted nematic liquid crystal cell in the light shutter thereof.

DESCRIPTION OF THE PREFERRED EMBODIMENT

Figure 8:
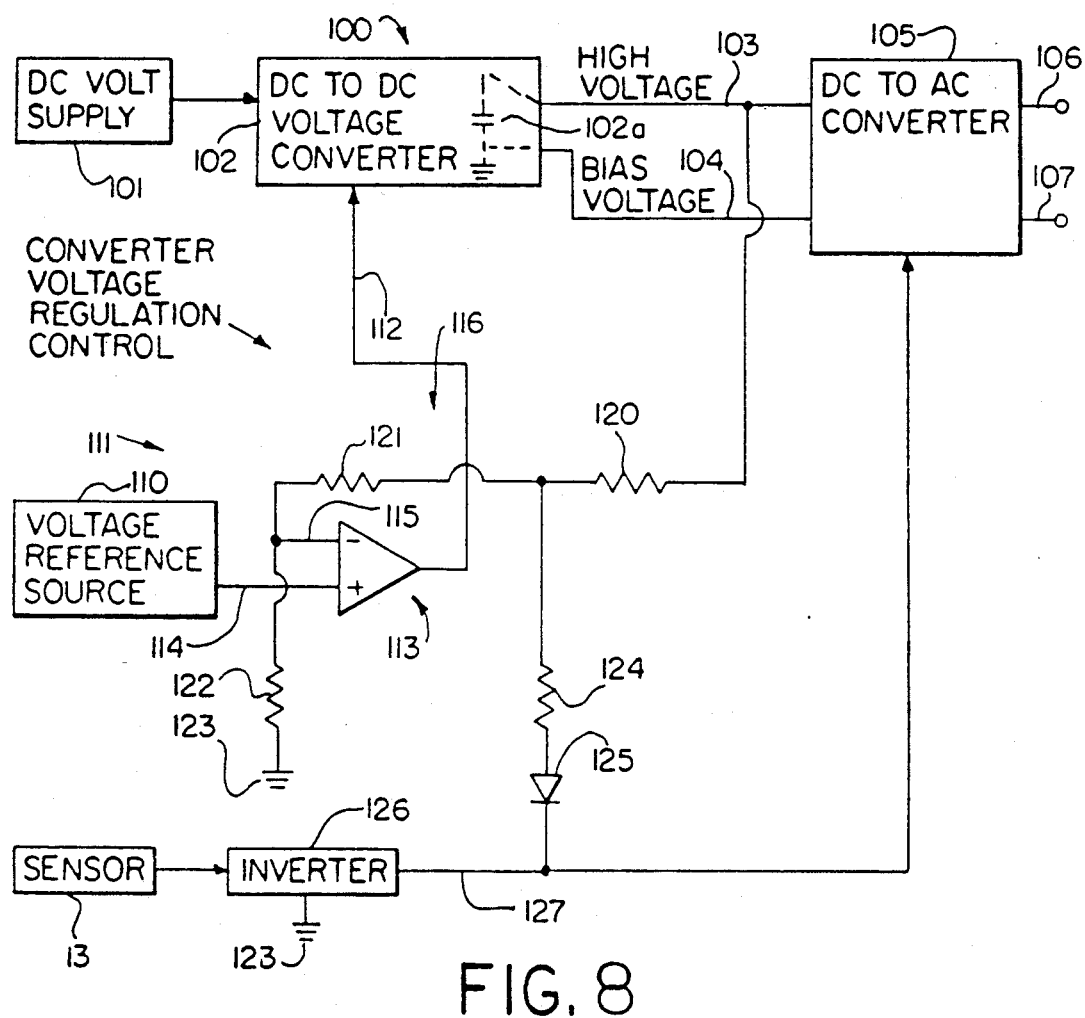
FIG. 8 is a schematic circuit diagram of a circuit for driving a surface mode birefringent liquid crystal cell in accordance with the invention at voltage levels for biasing, initiating and sustaining modes of operation, respectively.

The present invention is described in detail herein with respect to protection of the eyes of an individual from the light or other electromagnetic energy emitted during electric arc welding operation. However, it will be appreciated that the invention may be employed for other eye protection purposes and to protect other animate and inanimate objects. Also, the combination light shutter and variable polarizer parts of the present invention may be employed in goggles, in large area light transmissive devices, such as windshields or windscreens, of vehicles, etc., according to the present invention.

Referring, now, in detail to the drawings, and initially to FIG. 1, protection for the eyes 9 of a person is provided by a welding helmet 10 according to the invention. The welding helmet includes a protective shield plate 11 of molded plastic, metal or other material intended to protect the face, eyes, head and/or other parts of a person. The shield plate 11 may be of other design, material, and so on; it may be the frame of a pair of goggles, for example, and so forth. A controllable lens assembly 12 is located in the shield plate 11, preferably in an opening 12a provided therefore.

The lens assembly 12 is intended to control the transmission of light therethrough so that maximum and minimum light transmission conditions or operative modes can be obtained, e.g., when welding is or is not occurring. When welding is not occurring it is desirable to provide a maximum light transmission condition; and when it is occurring, it is desirable to minimize transmission to protect the eyes of the person performing the welding.

Control of the lens assembly 12 preferably is automatic. As an example, a photosensitive device 13, such as a photocell or photosensor, may be placed relative to the lens assembly 12 to sense the impingement of light due to welding on the device 13 and, therefore, on the lens assembly 12. An electrical circuit 14 (seen in FIG. 2) may be responsive to such sensing of such light to cause the lens assembly 12 to assume the light blocking or minimum light transmission mode. Exemplary circuitry and light sensing apparatus are described in one or more of the above-referenced patents. Alternatively, the sensing of the welding operation may be by sensing the magnetic field or electric field that is developed by the power supply employed to carry out the welding process. Apparatus for such sensing also is described in one or more of such above-referenced patents. Such sensing apparatus and circuitry may be employed in the present invention.

Referring to FIG. 2, the lens assembly 12 includes a fixed notch filter 20, a fixed plane polarizer 21, an optional optical compensating filter 22, a liquid crystal cell 23, a second fixed plane polarizer 24, and an electrically controlled variable polarizer 25. Associated with the lens assembly 12 is the electrical circuit 14, which is described in detail below. Such electric circuit is operative to apply electrical inputs to the liquid crystal cell 23 and to the electrically controlled variable polarizer 25 in the manner described in greater detail below. The liquid crystal cell 23 together with the polarizers 21, 24 will be referred to below collectively as a light shutter 26, the purpose of which is to provide the primary controllable light attenuation or transmission of the lens assembly 12 as is described elsewhere herein.

The relative directions of polarization of the polarizers 21 and 24, the direction of the axis of an exemplary surface mode birefringent liquid crystal cell 23' (FIGS. 2 and 3A, 3B) and of the optional wave plate 22 are depicted by arrows shown in FIG. 2. (Primed reference numerals in the several figures designates parts, components or elements that generally may be inserted or substituted for parts, components or elements designated elsewhere in the drawing, e.g., in other figures, by unprimed or other primed numbers Therefore, although reference numeral 23' does not appear in FIG. 2, reference numeral 23 does appear there; and by referring herein to reference numeral 23', in is intended to identify part 23' from FIGS. 3A and 3B as substituted in FIG. 2 for the element identified by reference numeral 23 therein.) The vertical arrows represent vertical polarization direction for plane polarized light derived from light 27 that is propagating through the lens assembly 12; the arrows that are drawn at angles other than vertical represent relative angles that would be relatively crossed to the vertical direction of polarization of the plane polarizers 21, 24 as light propagates in the direction represented by arrow 27.

The notch filter 20 may be a conventional filter of the type used on conventional fixed transmission lens welding helmets. Such notch filter 20 reduces the ultraviolet light and/or infrared light that may otherwise cause degradation of various portions of the liquid crystal cell components, e.g., the liquid crystal material itself and/or pleochroic dye that may be included therein, and/or the polarizers, depending on the nature thereof. The notch filter 20 also preferably has a hard glass, quartz or other material outer surface 28 to provide increased durability, protection from damage, etc. for the lens assembly 12.

The fixed polarizers 21 and 24 preferably are conventional plane or linear polarizers. Such polarizers are oriented insofar as plane or direction of polarization thereof is concerned in a relationship to each other (and possibly also relative to the liquid crystal cell 23 itself) that is cooperative with the liquid crystal cell 23 such that in the presence of a prescribed input to the cell 23 that would be supplied when minimum light transmission is desired, in fact minimum light transmission occurs through the light shutter formed of the combination of the polarizers 21 and 24 and the liquid crystal cell 23. Likewise, such orientation considerations are such that when it is desired to increase light transmission and reduced electrical input is supplied to the liquid crystal cell 23, in fact increased transmission does occur. If desired, the polarizers 21, 24 may be other types of polarizers that are operative to provide the light shutter functions in cooperation with the liquid crystal cell 23, as is described herein.

In the preferred embodiment the polarizers 21 and 24 are crossed at an angle that exceeds about 45 degrees and may be as much as 90 degrees, i.e., be fully Crossed at an orthogonal relationship. Depending on the nature of the liquid crystal cell 23, e.g., if it is of the birefringent type that does go from no rotation to a full 90 degrees rotation or in any event from some rotation to 90 degrees more rotation of polarized light, the relative arrangement of polarizers 21 and 24 with respect to each other and/or with respect to the liquid crystal cell may be varied to achieve the desired minimum and maximum or increased and reduced light transmission conditions when electrical voltage and thus electric field is not applied or is applied, respectively.

In the preferred embodiment the liquid crystal cell 23 is of the surface mode birefringent type described in the above-referenced patents. However, if desired, the liquid crystal cell 23 may be of another birefringent type, a twisted nematic liquid crystal cell (including supertwist type devices), or some other liquid crystal or other device which is operative in a satisfactory time in response to a prescribed input to reduce transmission of light and also operative in another mode to provide for increased transmission of light. The surface mode birefringent liquid crystal cell 23 is preferred because it has a speed of operation that is one or more orders of magnitude faster than the conventional twisted nematic liquid crystal cell.

An exemplary surface mode type of birefringent liquid crystal cell 23' is illustrated in FIGS. 3A and 3B. Such cell 23' includes a layer of liquid crystal material 30 sandwiched between a pair of transparent plates 31, 32 of glass, plastic, or the like. Transparent electrodes 33, 34 are on the interior surfaces of the plates to apply electric field E across the liquid crystal material. The interior surfaces also may have additional liquid crystal aligning coatings thereon. In the absence of electric field of suitable strength the liquid crystal may assume an alignment schematically depicted in FIG. 3A to increase retardation of one of the quadrature components of the polarized light transmitted through the liquid crystal cell 23' relative to the other quadrature component of such polarized light, thus effectively rotating the plane of polarization of the transmitted light. However, in the presence of the suitable electric field, as is shown in FIG. 3B, the liquid crystal tends to align with respect to the field to reduce such retardation and rotation As described in greater detail in the above-referenced patents, the changing of alignment of liquid crystal structure or directors in the surface mode liquid crystal cell 23' primarily occurs at the interior surfaces of the plates 31, 32; and, therefore, relatively fast operation occurs, especially in response to application of the suitable electric field.

The wave plate 22 may be employed to compensate for residual rotation of plane of polarization or excess retardation by a birefringent liquid crystal cell 23, 23' due to the fact, for example, that all of the liquid crystal material in such cell would not line up in the manner illustrated in FIG. 3B. It is known, for example, that the liquid crystal material that is directly in engagement with the surfaces of the plates 31, 32 would not fully align with such an applied field; and, therefore, some retardation would occur even when an electric field is applied across such a liquid crystal cell.

The electrically controlled variable polarizer 25 is operative to act as a linear or plane polarizer in the voltage off condition, i.e., when no voltage or electric field is supplied thereto; and to operate as a non-polarized device or fixed optical filter that does not have polarization function in the voltage on or field on condition. Moreover, the variable polarizer 25 is oriented such that the plane or direction of polarization thereof is related to the plane of polarization of the most proximate polarizer 24 thereto in the optical path of the lens assembly 12, as to be operative to tend to block light transmission when the polarizer 25 is in the polarizing mode thereof. Therefore, if power were lost to the controlled variable polarizer 25, which more than likely would occur at the same time that power may fail to the liquid crystal cell 23 of the light shutter, then such variable polarizer 25 in cooperation with the polarizer 24 would tend to reduce transmission of light through the lens assembly 12. Such reduced transmission preferably is on the order of one or several, e.g., four, shades different (i.e., more transmitting) than would be the case if there were suitable power to the liquid crystal shutter cell 23. Thus, the effectiveness or efficiency of the variable polarizer 25 may be less than a conventional fixed plane polarizer and/or it may be oriented relative to the plane polarizer 24 so as to achieve transmission of some light therethrough in the absence of power thereto but still to provide some blocking of light transmission in order to permit the user to see therethrough.

One example of a controlled variable polarizer 25' is illustrated in FIGS. 4A and 4B. Such polarizer 25' includes plural elongate volumes 40 of liquid crystal material 41 in a containment medium 42, as is described in one or more of the above-referenced patents. The liquid crystal material may include pleochroic dye 43 in guest host relation therewith. In the absence of an electrical field, the liquid crystal (and pleochroic dye, if used) align due to interaction with the surfaces of the volumes along the length or long axes of the elongate volumes. In such orientation the liquid crystal material and/or the dye tends to absorb or to block transmission of light that has an electric vector in a particular direction and to pass the light that has an electric vector in the relatively orthogonal direction; thus, the device 25' then acts as a plane polarizer, as is illustrated in FIG. 4A. In the presence of an electric field E of suitable magnitude supplied across the electrodes 44, 45, the liquid crystal (and dye, if used) aligns with respect to the field, as is illustrated in FIG. 4B, and polarization function decreases.

Alternatively, another example of a controlled variable polarizer 25'' is illustrated in FIGS. 5A and 5B. Such polarizer 25'' is in the form of a conventional twisted nematic liquid crystal cell 50 that includes nematic liquid crystal material 51 between a pair of parallel plates 52, 53 (of glass or other suitable material that have a surface alignment means to cause the liquid crystal material structure or directors to undergo a twist when no electric field E is applied, as is well known. Accordingly, such plates 52, 53 may have an alignment layer thereon which is rubbed in a straight direction and the directions of the two plates when placed in overlying relationship are perpendicular to each other to cause the desired twist in the nematic liquid crystal material and guest pleochroic dye 54 therein when in the absence of an electric field. Such plates 52, 53 also preferably are coated with an electrically conductive material (electrodes) on the inner surfaces to apply electric field.

When the liquid crystal material 51 and pleochroic dye 54 that is in guest host relationship with the liquid crystal material are in such twisted orientation the device 25'' tends to function as a polarizer, as is depicted in FIG. 5A. However, in the presence of a suitable electric field E supplied across the electrodes 55, 56, as is illustrated in FIG. 5B, the liquid crystal material and dye align with respect to the field and the polarization function decreases or is eliminated.

In accordance with the present invention other types of electrically controlled variable polarizers may be employed for the variable polarizer 25 in the lens assembly 12. One example is a surface mode liquid crystal material host with pleochroic dye as the guest material. Another example is an NCAP type of liquid crystal scattering device and/or absorbing device of the type disclosed in U.S. Pat. Nos. 4,435,047 and/or 4,556,289. An example of such an NCAP type of variable liquid crystal device 25''' is depicted in FIGS. 6A and 6B. As is seen in FIG. 6A, in the absence of an electric field, the liquid crystal material 57 (and pleochroic dye if contained therein) in volumes 58 in containment medium 59 assumes a curvilinear alignment causing light incident thereon to be scattered and/or absorbed. However, in the presence of an electric field E applied across the liquid crystal material, the liquid crystal material tends to align with respect to the field to reduce scattering and/or absorption of light. Therefore, it will be appreciated that if the variable liquid crystal device 25''' were receiving voltage (across electrodes 55', 56'), it would not effect attenuation of light incident thereon; but in the absence of voltage, e.g., due to a power failure, incident light would be scattered and/or absorbed so as to reduce the intensity of the light that would be received by the eyes 9.

The objective of such variable liquid crystal device 25 is to prevent full light from reaching the eyes 9, for example, in the event of a power failure. Such guest-/host surface mode liquid crystal cell may be similar to the surface mode birefringent liquid crystal cell of the type described above but being operative like a dyed twisted nematic liquid crystal cell selectively to provide polarization function or not. The NCAP type of device may be operative to transmit or to absorb light or to transmit or to scatter light, both without concern for the direction of polarization of incident light, depending on whether or not, respectively, suitable electric field is applied thereto.

Referring back to FIG. 2, the electric circuit 14 includes an electric supply 60, which has one or more amplifiers, batteries, control circuits, threshold detector circuits, etc., a number of which are depicted in the above-referenced patents. Generally, the electric supply 60 is responsive to the detecting of a prescribed input by the photosensor 13, such as the occurrence of light produced as a result of a welding arc or the like, to supply a voltage on line 61 via a controllable switch 62 to the liquid crystal cell 23 to cause the light shutter of that cell in combination with the polarizers 21, 24 to attenuate the light transmitted therethrough. The line 61 is an electrical conductor which is coupled to one of the electrodes of the 33 or 34, the other electrode being coupled to complete a circuit via line 63, e.g., to ground 64 or back to the electric supply 60, for developing the electric field by the respective pair of electrodes.

Moreover, the electric supply 60 is coupled via electrical conductor or line 65 and a selectively operable switch 66 to one of the electrodes 44 or 55 of the variable polarizer 25, 25', or 25". The other electrode 45 or 56 is coupled to complete an electric circuit via conductor 67 either to ground or back to the electric supply 60.

Associated with the electric supply 60 in the electric circuit 14 are a timer 70, a high/low voltage control circuit 71 and means 72 for operating the switch 62 selectively to apply or not a voltage to the liquid crystal cell 23. Such switch 62 is shown as a mechanical switch; however, it will be appreciated that the switch 62 may be an electronic switch that is operated by the electric supply 14 selectively to supply voltage of desired magnitude to the liquid crystal cell. Various electronic switches 62, such as transistor switches, field effect transistors, etc., are well known and may be used in the context of the present invention to provide the desired voltage and/or voltages with the desired speed of response. With the switch 62 being an electronic one, then, the means for controlling such switch may be an electrical conductor on which a suitable signal is applied to indicate the closure or not of the switch 62 and/or the magnitude of the voltage to be applied by the switch 62 to the liquid crystal cell. For example, voltages of different magnitudes may be supplied to the switch 62 on respective conductors 73, 74 from the electric supply 60.

In the electric supply 60 may be a conventional threshold detector circuit to detect when the output from the photosensor 13 indicates the receiving thereby of incident electromagnetic energy of a character that should require the liquid crystal shutter 26 to block transmission or to reduce transmission of light therethrough. Such threshold detector preferably is coupled to the timer 70, which may be a conventional electronic timer, to trigger the timing of a prescribed period. During such timed prescribed period, the timer provides an output to the high/low voltage control 71 to cause the latter to operate a switching circuit 81 in the electric supply 60 to operate the switch 62 to provide relatively high voltage to the liquid crystal cell 23. After the timer 70 times out, i.e., the prescribed period expires, the high/low voltage control 71 would operate the switching circuit 81 to throw the switch 62 or otherwise to operate that switch to cause a reduced voltage to be supplied to the liquid crystal cell 23 to continue to hold the light shutter 26 in the light blocking, dark operative mode. When the photosensor 13 no longer senses the input of electromagnetic energy which requires attenuation by the liquid crystal shutter 26, the electric supply would cut off power to the liquid crystal cell 23 or otherwise may operate that liquid crystal cell in manner to increase light transmission through the liquid crystal shutter 26.

At all times the electric supply 60 would be intended to provide adequate voltage to the variable polarizer 25, without regard to whether or not voltage is being supplied to the liquid crystal cell 23. Therefore, operation of the variable polarizer 25 is substantially independent of operation of the light shutter 26. In the event that power were lost to the light shutter so that it would stop attenuating light, it is likely that power also would be lost to the variable polarizer 25. Therefore, under such powerless condition the variable polarizer 25 would become polarizing and would cooperate with the polarizer 24 to attenuate light transmitted through the lens assembly 12.

From the foregoing, then, it will be appreciated that the lens assembly 12 is operative quickly to attenuate light using the primary light attenuator thereof, namely the light shutter 26, when such attenuation is required. Also, the lens assembly 12 is operative to maintain a reduced level of attenuation, but nevertheless attenuation and not full transmission, when in a failure mode due to loss of the source of electric energy from the electric supply 60, for example. Such reduced level of attenuation is effected by the cooperative effort of the polarization function of the variable polarizer 25 and the polarizer 24.

An example of a circuit 100 for use in the electrical circuit 14 of the invention is depicted in FIG. 8. The circuit 100 is operable to drive a surface mode type of birefringent liquid crystal cell 23 of the liquid crystal shutter 26 at a bias voltage, initiating voltage and sustaining voltage. The bias voltage may be of, for example, about 4 volts to maintain a maximum clear state or condition of the light shutter 26, The initiating voltage may be of, for example, about 42 volts to initiate reorientation of the liquid crystal structure to achieve a dark state. The sustaining voltage may be, for example, a value between the bias and initiating voltages to maintain a dark condition of the light shutter 26 after initiation of the dark condition, as is described elsewhere herein.

Preferably the initiating voltage is a pulse or is a relatively short duration voltage of, for example, from several microseconds to several milliseconds, depending, for example, on the nature of the liquid crystal materials, dimensions, temperatures expected, etc. of the liquid crystal Cell 23. In any event, the duration of such initiating voltage and the magnitude thereof preferably are adequate to cause a relatively rapid high speed reorientation of the liquid crystal structure or directors in the liquid crystal cell 23 adequate to cause the desired darkened condition of operation of the light shutter 26.

The circuit 100 is generally of the type disclosed in copending U.S. patent application Ser. No. 07/365,167, filed June 12, 1989, the entire disclosure of which hereby is incorporated by reference.

The circuit 100 is illustrated in detail in FIG. 8. The circuit 100 includes a DC voltage supply 101 of, for example, 5 volts to 12 volts. A DC to DC converter 102 converts the DC voltage from the supply 101 to a relatively high voltage, say about 42 volts, and to a relatively low voltage, say about 4 volts, which are provided, respectively, on the lines 103, 104 to a DC to AC converter 105. The DC to DC converter 102 may include a capacitor circuit 102a schematically shown in FIG. 8 to provide a voltage storage function and from which in particular the high voltage is provided to line 103. The output from the DC to AC converter 105 is an AC signal supplied on lines 106, 107 to respective electrodes of the liquid crystal cell 23.

A voltage reference source 110 provides a source of reference potential for a converter regulation control circuit 111. Such control 111 provides a signal on line 112 to provide a stabilized regulated voltage output, particularly the high voltage output on line 103. To provide such regulation, the control 111 includes a comparator circuit 113 which compares the voltage from the reference source 110 at input 114 with a voltage at input 115 that is derived from the high voltage line 103. If the signal from the source 110 on input 114 exceeds the signal on input 115, then the signal on line 112 causes the DC to DC converter 102 to increase the output on line 103. If the signal on input 115 exceeds the signal on input 114, then the signal produced by the comparator 113 on line 112 is such as to cause the converter 102 to stop trying to increase the voltage on line 103. The converter 112 then waits until it receives an input from the comparator 113 calling for the converter again to try to increase such voltage on line 103. In this way, the converter effectively maintains a substantially uniform voltage level on high level line 103.

The source of the signal on input 115 is derived from a voltage divider circuit 116, which includes series connected resistors 120, 121 and 122 that are coupled between high voltage line 103 and ground 123. The voltage divider circuit 116 further may selectively include a resistor 124, depending on whether or not a diode 125 is reverse biased, as is described further below.

In the circuit 100 of FIG. 8 a sensor, such as the photosensor 13, is coupled to an inverter 126 to cause the output 127 from the inverter either to be at a logic 1 signal level or a logic 0 signal level. Such logic level is a function of whether or not the optical input to the sensor 13 exceeds a prescribed value, such as would occur during welding operation. In the preferred embodiment, the line 127 would be logic 0 when a clear condition of the light shutter 26 is desired so that a bias voltage on line 104 would be supplied by the DC to AC converter to the liquid crystal cell 23. However, the line 127 would be at a logic 1 level when a dark condition is desired, whereupon the DC to AC converter 105 would be called on to provide the high voltage signal derived from line 103 to the liquid crystal cell 23.

Operation of the circuit 100 is as follows. When the clear state or maximum transmission state of liquid crystal cell 23 is desired, the logic 0 at line 127 causes the diode 124 to be forward biased so that the resistor 124 is operative in the voltage divider circuit 116 with the resistors 120, 121, 122. Therefore, the input 115 to the comparator 113 is such as to cause the DC to DC voltage converter 102 to produce a maximum voltage on high voltage line 103; such voltage is stored in and supplied from a capacitor 102a, for example. However, when the inverter output on line 127 is logic 1 calling for darkened mode of the light shutter 26, the diode 125 is reverse biased, thus taking resistor 124 operatively out of the voltage divider circuit 116. Therefore, the signal provided to input 115 of the comparator 113 will be such as to call for a reduced voltage level on high voltage line 103. Such reduced voltage level on high voltage line 103 is the sustaining voltage mentioned above.

There is a finite amount of time for the voltage on line 103 to drop down from the high voltage level to the sustaining voltage level; and during that time the high voltage level is supplied to the liquid crystal cell 23 via the DC to AC converter 105 as the initiating voltage described above Dissipation or dropping down of the initiating voltage to the sustaining voltage level would be a function of the effective resistance of the circuitry coupled with the capacitor 102a, for example, according to conventional RC time constant discharge considerations. Summarizing operation of the lens assembly 12, then, such lens assembly is maintained in the clear or non-attenuating condition by the application of a low voltage to the liquid crystal cell 23 or alternatively no voltage being applied to the liquid crystal cell 23. A sustaining voltage is applied to the controlled variable polarizer 25, such as from about 3 volts to about 8 volts. However, when a welder strikes an arc, the electronic circuit 14 applies a surge of high voltage, e.g., on the order of from about 20 volts to about 40 volts, to the liquid crystal cell 23 causing the directors thereof to reorient and the lens assembly 12 to darken rapidly. After a few microseconds (or perhaps milliseconds, if desired), the voltage to the liquid crystal cell 23 is reduced to a level that sustains the desired dark condition. The extent of such dark condition can be controlled, i.e., increased or decreased, by increasing or decreasing the magnitude of the voltage directed by the electric supply 60 to the liquid crystal cell. Such change of voltage may be under control of an amplifier 80 in the electronic supply and a manually adjustable potentiometer 90 or other control or automatically as a function of some sensed parameter. Such extent of dark condition also can be controlled further by changing the voltage to the variable polarizer 25, which acts in cooperation with the polarizer 24 to provide a light attenuation control function.

Briefly referring to FIG. 7, a modified lens assembly 12' is illustrated. The lens assembly 12' is substantially the same as the lens assembly 12 except that the liquid crystal cell 23'''' in the lens assembly 12' is a twisted nematic liquid crystal cell of known type. Operation of the lens assembly 12' is substantially the same as the operation described above except that the rotation or not of the plane of polarization of light incident on the liquid crystal cell 23'''' is a result of conventional operation of the liquid crystal cell.

STATEMENT OF INDUSTRIAL APPLICATION

From the foregoing, then, it will be appreciated that the present invention is operative to provide protection of the eyes of an individual during welding process and/or during other circumstances in which the eyes may otherwise be subjected to relatively high intensity electromagnetic energy or the like.

We claim:

1. A light control device, comprising a light shutter including a pair of polarizers and a liquid crystal device operative in response to a prescribed input to control transmission of light therethrough, and a variable polarizer optically aligned with respect to said light shutter and operative to control light transmitted therethrough in response to a prescribed input.

2. The device of claim 1, wherein said pair of polarizers are plane polarizers.

3. The device of claim 2, said plane polarizers being generally crossed at an angle other than parallel.

4. The device of claim 3, said plane polarizers being crossed at an angle exceeding 45 degrees.

5. The device of claim 4, said plane polarizers being crossed at an angle of approximately 90 degrees.

6. The device of claim 1, said liquid crystal device comprising a birefringent liquid crystal cell.

7. The device of claim 6, further comprising a compensating wave plate optically aligned with respect to said birefringent liquid crystal cell.

8. The device of claim 6, said liquid crystal device comprising a surface mode birefringent liquid crystal cell.

9. The device of claim 8, further comprising a compensating wave plate optically aligned with respect to said birefringent liquid crystal cell to compensate for residual birefringence thereof in at least one operative condition.

10. The device of claim 1, said liquid crystal device comprising a twisted nematic liquid crystal cell.

11. The device of claim 1, said variable polarizer comprising a polarizer on demand liquid crystal device.

12. The device of claim 11, said polarizer on demand liquid crystal device comprising plural elongate volumes of liquid crystal material in a containment medium, said liquid crystal material being aligned due to interaction with the surfaces bounding such volumes to cause polarization function in the absence of a field input and being responsive to such input to align with respect thereto to reduce such polarization function.

13. The device of claim 11, said volumes of liquid crystal material also including pleochroic dye in such liquid crystal material and operative to align with respect thereto in guest host relationship.

14. The device of claim 1, said variable polarizer comprising a dyed twisted nematic liquid crystal cell.

15. The device of claim 1, further comprising circuit means for applying a prescribed input to said liquid crystal device and variable polarizer.

16. The device of claim 15, said circuit means comprising means for applying an input to said variable polarizer to prevent polarization function thereof; and said variable polarizer being responsive to reduction or removal of such input to increase polarization function 17. The device of claim 16, said light shutter being operative in response to an applied input to assume a condition to reduce transmission of light therethrough.

18. The device of claim 17, said variable polarizer being cooperative when providing such polarization function with at least part of said light shutter to block at least some light transmission upon removal or reduction of such input to said variable polarizer.

19. The device of claim 1, said light shutter being operative in response to an applied input to assume a condition to reduce transmission of light therethrough, and further comprising circuit means for supplying electrical input to said light shutter to control light transmission characteristics thereof.

20. The device of claim 19, said circuit means including an electrical circuit for initially supplying a relatively large voltage to said light shutter rapidly to cause such shutter to assume a reduced light transmission mode of operation and for subsequently providing a reduced holding voltage to maintain said light shutter in such holding mode.

21. The device of claim 20, further comprising means for sensing the occurrence of a welding condition, said means for sensing causing operation of said circuit means to cause said light shutter to assume a reduced light transmission mode upon sensing such welding condition.

22. The device of claim 1, further comprising circuit means including an electrical circuit for initially supplying a relatively large voltage to said light shutter rapidly to cause such shutter to assume a reduced light transmission mode of operation and for subsequently providing a reduced holding voltage to maintain said light shutter in such holding mode.

23. The device of claim 1, further comprising a notch filter to reduce incident electromagnetic energy that tends to degrade other components of the device.

24. The device of claim 23, said notch filter comprising a filter for blocking transmission of ultraviolet and/or infrared energy.

25. The device of claim 1, further comprising a hard surface on the outside of said light shutter and/or variable polarizer to protect the same from damage.

26. The device of claim 1, further comprising circuit means for supplying a prescribed input to said shutter to alter the light transmission characteristics thereof, said circuit means including adjustable means for adjusting a characteristic of such prescribed input thereby to alter the shade or shade level of light transmission operation of said liquid crystal shutter.

27. A welding helmet comprising a protective shield, and a light control device, comprising a light shutter including a pair of polarizers and a liquid crystal device operative in response to a prescribed input to control transmission of light therethrough, and a variable polarizer optically aligned with respect to said light shutter and operative to control light transmitted therethrough in response to a prescribed input.

28. An eye protection apparatus comprising a lens assembly for positioning in front of the eyes, said lens assembly including a light shutter having a pair of polarizers and a liquid crystal device operative in response to a prescribed input to control transmission of light therethrough, and a variable polarizer optically aligned with respect to said light shutter and operative to control light transmitted therethrough in response to a prescribed input.

29. A method for protecting the eyes of an individual, comprising directing light to a light shutter which includes a pair of polarizers and a liquid crystal device, supplying a prescribed input to control transmission of light through such device, and directing light transmitted through such light shutter through a variable polarizer operative to control light transmitted therethrough in response to a prescribed input.

30. A light control device, comprising a light shutter including a pair of polarizers and a liquid crystal device operative in response to a prescribed input to control transmission of light therethrough, and a variable liquid crystal device optically aligned with respect to said light shutter and operative to control light transmitted therethrough in response to a prescribed input and including a plurality of volumes of liquid crystal material in a containment medium operative to effect scattering or absorption of light in the absence of a field input and to reduce such scattering or absorption in the presence of such field input.

31. The device of claim 30, said volumes of liquid crystal material also including pleochroic dye in such liquid crystal material and operative to align with respect thereto in guest host relationship.

32. The device of claim 30, said liquid crystal device comprising a birefringent liquid crystal cell.

33. The device of claim 32, said liquid crystal device comprising a surface mode birefringent liquid crystal cell.

34. The device of claim 33, further comprising a compensating wave plate optically aligned with respect to said birefringent liquid crystal cell to compensate for residual birefringence thereof in at least one operative condition.

35. The device of claim 30, said light shutter being operative in response to an applied input to assume a condition to reduce transmission of light therethrough, and further comprising circuit means for supplying electrical input to said light shutter to control light transmission characteristics thereof.

36. The device of claim 35, said circuit means including an electrical circuit for initially supplying a relatively large voltage to said light shutter rapidly to cause such shutter to assume a reduced light transmission mode of operation and for subsequently providing a reduced holding voltage to maintain said light shutter in such holding mode.

37. The device of claim 35, wherein said circuit means includes adjustable means for adjusting a characteristic of such electrical input to alter the shade or shade level of light transmission through said light shutter.

38. The device of claim 30, further including circuit means for providing such field input to said variable liquid crystal device.

39. A method for protecting the eyes of an individual from electromagnetic energy; comprising positioning between the eyes of the individual and a source of such energy a variable polarizer and a light shutter which includes a pair of polarizers and a liquid crystal device; supplying a prescribed input to such variable polarizer to control transmission of energy therethrough; and supplying a prescribed input to such liquid crystal device to control transmission of such energy through such light shutter.

* * * * *